United States Patent
Griffin et al.

(10) Patent No.: US 6,652,508 B2
(45) Date of Patent: Nov. 25, 2003

(54) INTRAVASCULAR MICROCATHETER HAVING HYPOTUBE PROXIMAL SHAFT WITH TRANSITION

(75) Inventors: Stephen Griffin, Sunnyvale, CA (US); Greg Mirigian, Dublin, CA (US); Tina Ye, San Jose, CA (US)

(73) Assignee: SciMed Life Systems, Inc., Maple Grove, CA (US)

( * ) Notice: Subject to any disclaimer, the term of this patent is extended or adjusted under 35 U.S.C. 154(b) by 61 days.

(21) Appl. No.: 10/007,536

(22) Filed: Nov. 9, 2001

(65) Prior Publication Data

US 2003/0093059 A1 May 15, 2003

(51) Int. Cl.[7] ............................................. A61M 25/00
(52) U.S. Cl. ........................ 604/526; 604/525; 604/524
(58) Field of Search ................................. 604/523–527, 604/264, 93.01, 96.01; 606/191, 194; 600/433–435, 585, 139, 140, 143; 138/118, 123, 124, 129, 134, 137, 140

(56) References Cited

U.S. PATENT DOCUMENTS

| | | |
|---|---|---|
| 3,467,101 A | 9/1969 | Fogarty et al. |
| 4,385,635 A | 5/1983 | Ruiz |
| 4,430,083 A | 2/1984 | Ganz et al. |
| 4,547,193 A | 10/1985 | Rydell |
| 4,569,347 A | 2/1986 | Frisbie |
| 4,690,175 A | 9/1987 | Ouchi et al. |
| 4,801,297 A | 1/1989 | Mueller |
| 4,925,445 A | 5/1990 | Sakamoto et al. |
| 4,960,410 A | 10/1990 | Pinchuk |
| 4,998,923 A | 3/1991 | Samson et al. |
| 5,047,045 A | 9/1991 | Arney et al. |
| 5,069,226 A | 12/1991 | Yamauchi et al. |
| 5,095,915 A | 3/1992 | Engelson |
| 5,100,381 A | 3/1992 | Burns |
| 5,114,402 A | 5/1992 | McCoy |
| 5,147,315 A * | 9/1992 | Weber .................. 604/164.09 |
| 5,156,594 A | 10/1992 | Keith |
| 5,180,376 A | 1/1993 | Fischell |
| 5,213,111 A | 5/1993 | Cook et al. |
| 5,318,526 A | 6/1994 | Cohen |

(List continued on next page.)

FOREIGN PATENT DOCUMENTS

| | | |
|---|---|---|
| DE | 4104092 | 8/1991 |
| EP | 0 063 859 A2 | 3/1982 |
| EP | 0 102 685 B1 | 5/1982 |
| EP | 0 411 118 A1 | 3/1988 |
| EP | 0 370 785 A1 | 11/1989 |
| EP | 0 437 795 B1 | 12/1990 |
| EP | 0 594 201 B1 | 10/1993 |
| EP | 0 608 853 A2 | 1/1994 |
| EP | 0 631 791 B1 | 6/1994 |
| EP | 0 688 576 B1 | 6/1995 |
| EP | 0 778 039 A1 | 12/1996 |
| FR | 2713492 | 6/1995 |
| JP | 8257128 | 10/1991 |
| WO | WO 93/04722 | 3/1993 |
| WO | WO 96/38193 | 12/1996 |
| WO | WO 99/11313 | 3/1999 |

*Primary Examiner*—Brian L. Casler
*Assistant Examiner*—Cris L. Rodriguez
(74) *Attorney, Agent, or Firm*—Crompton, Seager & Tufte, LLC

(57) ABSTRACT

An intravascular catheter including a proximal stiff metallic tube and a distal flexible tube. A distal portion of the metallic tube has a portion removed to define a void (e.g., spiral slot) which decreases the stiffness of the metallic tube. A proximal portion of the distal flexible tube is disposed in the void to provide a secure connection and to blend the stiffness of the metallic proximal tube and the flexible distal tube without significantly increasing profile.

17 Claims, 2 Drawing Sheets

U.S. PATENT DOCUMENTS

| | | | |
|---|---|---|---|
| 5,364,357 A | 11/1994 | Aase | |
| 5,381,782 A | 1/1995 | DeLaRama et al. | |
| 5,409,015 A | 4/1995 | Palermo | |
| 5,437,288 A | 8/1995 | Schwartz et al. | |
| 5,443,455 A | 8/1995 | Hergenrother et al. | |
| 5,452,726 A | 9/1995 | Burmeister et al. | |
| 5,454,787 A | 10/1995 | Lundquist | |
| 5,456,665 A | 10/1995 | Postell et al. | |
| 5,458,605 A | 10/1995 | Klemm | |
| 5,480,382 A * | 1/1996 | Hammerslag et al. | 604/528 |
| 5,497,785 A * | 3/1996 | Viera | 600/585 |
| 5,507,766 A | 4/1996 | Kugo et al. | |
| 5,531,719 A | 7/1996 | Takahashi | |
| 5,542,434 A | 8/1996 | Imran et al. | |
| 5,546,958 A | 8/1996 | Thorud et al. | |
| 5,549,552 A | 8/1996 | Peters et al. | |
| 5,569,200 A | 10/1996 | Umeno et al. | |
| 5,573,520 A | 11/1996 | Schwartz et al. | |
| 5,596,996 A | 1/1997 | Johanson et al. | |
| 5,636,642 A | 6/1997 | Palermo | |
| 5,716,410 A | 2/1998 | Wang et al. | |
| 5,720,724 A | 2/1998 | Ressemann et al. | |
| 5,722,424 A | 3/1998 | Engelson | |
| 5,741,429 A | 4/1998 | Donadio, III et al. | |
| 5,743,876 A | 4/1998 | Swanson | |
| 5,749,837 A | 5/1998 | Palermo | |
| 5,750,206 A | 5/1998 | Hergenrother et al. | |
| 5,769,796 A | 6/1998 | Palermo et al. | |
| 5,772,609 A | 6/1998 | Nguyen et al. | |
| 5,776,100 A | 7/1998 | Forman | |
| 5,780,807 A | 7/1998 | Saunders | |
| 5,782,809 A | 7/1998 | Umeno et al. | |
| 5,813,997 A | 9/1998 | Imran et al. | |
| 5,814,063 A | 9/1998 | Freitag | |
| 5,827,201 A | 10/1998 | Samson et al. | |
| 5,833,632 A | 11/1998 | Jacobsen et al. | |
| 5,836,893 A | 11/1998 | Urick | |
| 5,843,031 A | 12/1998 | Hermann et al. | |
| 5,843,050 A | 12/1998 | Jones et al. | |
| 5,860,938 A | 1/1999 | Lafontaine et al. | |
| 5,911,715 A * | 6/1999 | Berg et al. | 604/525 |
| 5,916,177 A | 6/1999 | Schwager | |
| 5,916,178 A | 6/1999 | Noone et al. | |
| 5,921,956 A | 7/1999 | Grinberg et al. | |
| 5,921,958 A | 7/1999 | Ressemann et al. | |
| 5,938,623 A | 8/1999 | Quiachon et al. | |
| 5,951,539 A | 9/1999 | Nita et al. | |
| 5,964,714 A | 10/1999 | Lafontaine | |
| 5,984,878 A | 11/1999 | Engelson | |
| 6,001,068 A | 12/1999 | Uchino et al. | |
| 6,004,279 A | 12/1999 | Crowley et al. | |
| 6,017,319 A | 1/2000 | Jacobsen et al. | |
| 6,019,736 A | 2/2000 | Avellanet et al. | |
| 6,024,764 A | 2/2000 | Schroeppel | |
| 6,027,863 A | 2/2000 | Donadio, III | |
| 6,036,670 A | 3/2000 | Wijeratne et al. | |
| 6,048,338 A | 4/2000 | Larson et al. | |
| 6,090,072 A | 7/2000 | Kratoska et al. | |
| 6,096,012 A | 8/2000 | Bogert et al. | |
| 6,102,890 A | 8/2000 | Stivland et al. | |
| 6,139,510 A | 10/2000 | Palermo | |
| 6,146,339 A | 11/2000 | Biagtan et al. | |
| 6,160,084 A | 12/2000 | Langer et al. | |
| 6,168,604 B1 | 1/2001 | Cano | |
| 6,183,443 B1 | 2/2001 | Kratoska et al. | |
| 6,193,706 B1 | 2/2001 | Thorud et al. | |
| 6,273,879 B1 | 8/2001 | Keith et al. | |
| 6,464,632 B1 * | 10/2002 | Taylor | 600/139 |
| 2001/0037085 A1 | 11/2001 | Keith et al. | |

* cited by examiner

INTRAVASCULAR MICROCATHETER HAVING HYPOTUBE PROXIMAL SHAFT WITH TRANSITION

FIELD OF THE INVENTION

The present invention generally relates to catheters. More specifically, the present invention relates to intravascular microcatheters.

BACKGROUND OF THE INVENTION

Intravascular catheters are used to diagnose and treat a wide variety of vascular diseases in various parts of the human vasculature. To access the cerebral vasculature, as well as other remote and tortuous vascular sites, it is desirable to have a catheter that has good navigational capabilities.

SUMMARY OF THE INVENTION

To address this need, the present invention provides, in one example, an intravascular microcatheter having a relatively stiff proximal shaft (e.g., super elastic hypotube) for pushability and torqueability. The microcatheter also includes a relatively flexible distal shaft portion (e.g., coil reinforced multi-layered gradient polymer tube) for trackability. To provide a smooth transition between the relatively stiff proximal shaft and the relatively flexible distal shaft, a transition region is provided by integrating portions of the proximal shaft and portions of the distal shaft in a manner that provides a secure connection and that minimizes profile increase. The result is a low profile microcatheter having superior response and control to navigate through tortuous vasculature to remote vascular sites.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
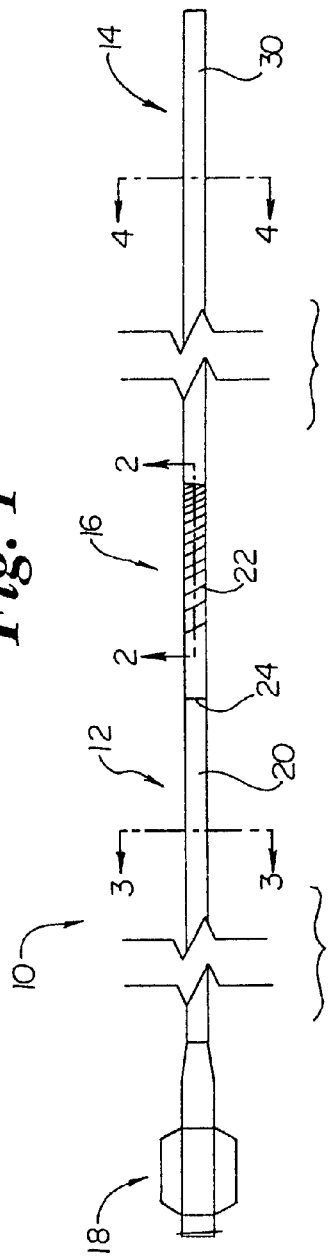
FIG. 1 is a schematic plan view of an intravascular microcatheter in accordance with an embodiment of the present invention.

Refer now to FIG. 1 which illustrates a catheter 10 in accordance with an embodiment of the present invention. For purposes of illustration only, the catheter 10 is shown in the form of an intravascular microcatheter, but the catheter 10 may comprise virtually any catheter used for intravascular applications. By way of example, the length, profile, pushability, trackability, and other performance characteristics of the microcatheter 10 may be selected to enable intravascular insertion and navigation to the cerebral vasculature.

In the embodiment illustrated, the microcatheter 10 may include a relatively stiff proximal portion 12 for pushability and torqueability. The microcatheter 10 may also include a relatively flexible distal portion 14 for trackability. The proximal shaft portion 12 may comprise a super elastic alloy (e.g., nitinol) hypotube 20, and the distal shaft portion 14 may comprise a coil reinforced multi-layer tube 30. To facilitate a smooth transition between the relatively stiff proximal shaft portion 12 and the relatively flexible distal shaft portion 14, a transition section 16 may be utilized as described in more detail hereinafter.

Figure 2:
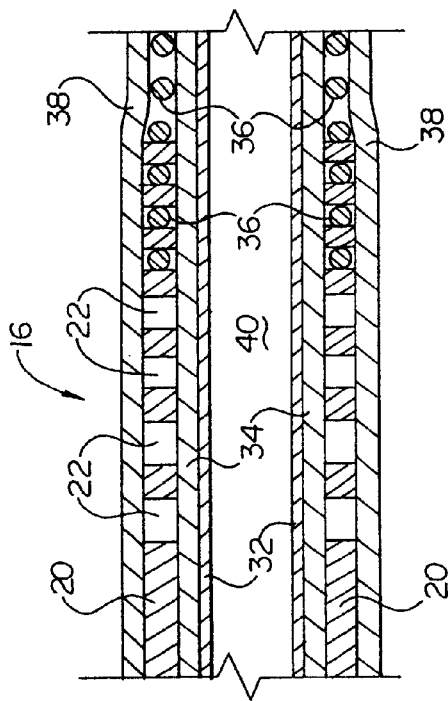
FIG. 2 is a longitudinal sectional view taken along line 2—2 in FIG. 1.
Figure 4:
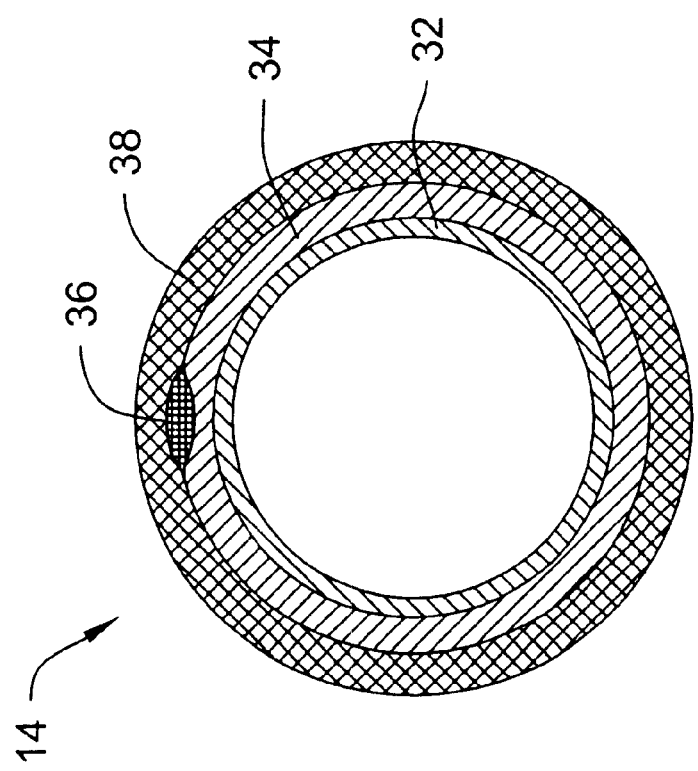
FIG. 4 is a cross-sectional view taken along line 4—4 in FIG. 1.
Figure 3:
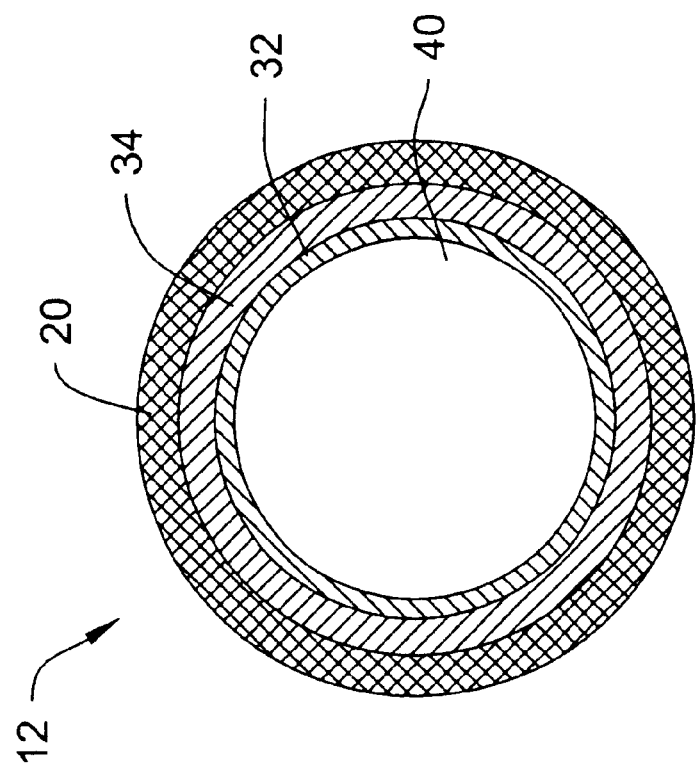
FIG. 3 is a cross-sectional view taken along line 3—3 in FIG. 1.

The microcatheter 10 may include a lumen 40 (as best seen in FIGS. 2–4) extending therethrough to facilitate the delivery of fluids (e.g., thrombolytic agents, radiopaque dye, saline, drugs, etc.) therethrough, and/or to facilitate the insertion of other medical devices (e.g., occlusive coils, guide wires, balloon catheters, etc.) therethrough. To provide access to the lumen 40 and to facilitate connection to ancillary devices, the microcatheter 10 may include a hub or manifold 18 connected to the proximal end of the proximal shaft portion 12. The lumen 40 may extend through the entire length of the microcatheter 10 (i.e., through hub 18, proximal shaft portion 12, mid-shaft transition portion 16, and distal shaft portion 14) to establish a path from a point outside the patient's body to a remote site within the patient's vascular system.

With reference to FIGS. 2–4, the proximal 12, distal 14, and transition 16 sections of the shaft will be discussed in more detail.

As mentioned above, the proximal shaft section 12 may include a metallic hypotube 20 formed of a super elastic material such as a nickel titanium alloy, or other suitable material such as stainless steel. For example, the hypotube 20 may comprise nitinol having a length of about 120–150 cm and a wall thickness of about 0.0015–0.004 inches. A portion of the distal end of the hypotube 20 may be removed to define one or more voids 22. In the example shown, the voids 22 comprise a helical or spiral slot cut into the wall of the hypotube 20 utilizing a suitable process such as laser cutting. The helical slot 22 may have a width of about 0.0002 inches or more, and may have a pitch which varies linearly from proximal to distal to gradually reduce the stiffness of the hypotube 20. For example, the distal 60 cm may be laser cut to define a helical slot 22, with the proximal segment having a pitch that gradually reduces from about 0.10 inches to about 0.001 inches, with the remaining distal segment having a constant/continuous pitch of about 0.001 inches. Alternatively, the pitch may gradually reduce through the distal segment as well.

Those skilled in the art will recognize that the voids 22 may comprise a variety of geometries, including without limitation, a continuous slot as shown, a series of slots or holes distributed around the circumference and length of the hypotube 20, etc. In addition, the voids 22 may extend completely through the wall of the hypotube 20 or may simply form a recess therein.

The distal shaft section 14 may include an inner liner 32 formed of a lubricious polymer such as PTFE or HDPE. An inner layer 34 comprising a polymer such as polyether block amide (e.g., PEBAX) may be placed over the inner liner 32. The outside diameter of the inner layer 34 may be approximately 0.001 inches smaller than the inside diameter of the hypotube 20 to allow the inner liner 32 and the inner layer 34 to be disposed therein. The inner liner 32 and the inner layer 34 may extend through the transition region 16 of the hypotube 20, or through the entire length of the hypotube 20 including the transition region 16 and the proximal shaft portion 12.

For example, the inner liner 32 and the inner layer 34 may extend through the entire length of the hypotube 20, with 30 cm extending beyond the distal end of the hypotube 20. With the assistance of a support mandrel disposed in the lumen of the combined inner liner 32 and inner layer 34, the same 32/34 may be inserted into the proximal end of the hypotube 20 and advanced until the distal end thereof extends 30 cm beyond the distal end of the hypotube 20. As it is being advanced, a suitable adhesive such as cyanoacrylate may be applied to the outer surface of the proximal 10 cm of the inner layer 34 for securement to the inside surface of the proximal end of the hypotube 20. At this time, the hub 18 may be connected to the proximal end of the hypotube shaft 20.

Optionally, a reinforcement layer 36 such as a single coil, multiple coils, or multiple interwoven coils (i.e., a braid) may be disposed over the combined inner liner 32 and inner layer 34 extending beyond the distal end of the hypotube 20. The reinforcement layer may comprise round wire or rectangular ribbon wire, for example. A proximal portion of the reinforcement layer 36 may be disposed in the voids 22 to provide a secure, low profile connection to the distal end of the hypotube 20, and to prevent migration of the reinforcement layer 36. For example, if the reinforcement layer 36 comprises a single coil and the voids 22 define a helical slot, the coil 36 may be wound into one or more of the distal slots.

Other portions of the distal composite shaft section 30 may be disposed in the voids 22 in addition to or in place of the coils 36. For example, a portion of the inner layer 34 and/or outer layer 38 may be disposed in the voids 22 to modify or enhance the connection between the distal composite shaft 30 and the proximal hypotube shaft 20.

An outer layer 38 formed of a suitable polymeric material may then be placed over the transition region 16 and the distal shaft section 14, and optionally over the proximal shaft section 12 as well. In particular, the outer layer 38 may extend from a point 24 on the hypotube 20 proximal of the spiral cut 22 to the terminal end of the combined inner liner 32, inner layer 34, and coil reinforcement layer 36. The outer layer may be formed of a flexible polymer such as polyether block amide (e.g., PEBAX), and may have a gradual transition in flexibility as provided by the gradient extrusion process described in co-pending patent application Ser. No. 09/430,327, entitled METHOD AND APPARATUS FOR EXTRUDING CATHETER TUBING, the entire disclosure of which is hereby incorporated by reference. By way of example, not limitation, the outer layer 38 may comprise a polyether block amide (e.g., PEBAX) polymer tube formed by gradient extrusion, with a durometer transitioning from 55D to 25D from proximal to distal. The gradient transition in the outer layer 38 provides superior flexibility, response, and control, while contributing to the smooth transition 16 from the relatively stiff proximal section 12 to the relatively flexible distal section 14. Alternatively, the outer layer 38 may comprise a polymer tube having a continuous durometer, or a series of connected polymer tubes having different durometers.

From the foregoing, it will be apparent to those skilled in the art that the present invention, in one exemplary embodiment, provides an intravascular microcatheter 10 having a relatively stiff proximal hypotube shaft 20 for pushability and torqueability, and a relatively flexible distal composite shaft 30 for trackability. To provide a smooth transition between the relatively stiff proximal shaft 12 and the relatively flexible distal shaft 14, a transition region 16 is provided by integrating portions of the proximal shaft (e.g., spiral cut 22 portion of the hypotube 20) and portions of the distal shaft (e.g., coil reinforcement 36) in a manner that provides a secure connection and that minimizes profile increase.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular catheter, comprising an elongate shaft having a proximal portion, a distal portion, and a transition region disposed therebetween, the proximal portion comprising a relatively stiff metallic tube, the distal portion comprising a relatively flexible tube including a coil reinforcement disposed between an inner layer and an outer layer, the transition portion comprising the metallic tube with at least a portion thereof removed to define at least one void, wherein a portion of the coil reinforcement is disposed in the void and wherein the outer layer extends proximally over the transition region.

2. An intravascular catheter as in claim 1, wherein the void decreases the stiffness of the metallic tube.

3. An intravascular catheter as in claim 2, wherein the void gradually decreases the stiffness of the metallic tube.

4. An intravascular catheter as in claim 3, wherein the void comprises a slot.

5. An intravascular catheter as in claim 4, wherein the slot forms a helix.

6. An intravascular catheter as in claim 1, wherein the metallic tube comprises a super elastic alloy.

7. An intravascular catheter as in claim 1, wherein the outer layer comprises a polymer tube having a gradient durometer.

8. An intravascular catheter as in claim 1, wherein the inner layer extends proximally into the transition region.

9. An intravascular catheter as in claim 8, wherein the inner layer extends proximally into the proximal portion.

10. An intravascular catheter, comprising an elongate shaft including a proximal stiff metallic tube having a distal portion, a distal flexible tube connected to and extending distally from the distal portion of the metallic tube, the flexible tube including a coil reinforcement disposed between an inner layer and an outer layer, the distal portion of the metallic tube having a portion removed to define at least one void which decreases the stiffness of the metallic tube, wherein a portion of he coil reinforcement is disposed in the void and wherein the outer layer extends proximally over the transition region.

11. An intravascular catheter as in claim 10, wherein the void gradually decreases the stiffness of the metallic tube.

12. An intravascular catheter as in claim 11, wherein the void comprises a slot.

13. An intravascular catheter as in claim 12, wherein the slot forms a helix.

14. An intravascular catheter as in claim 10, wherein the metallic tube comprises a super elastic alloy.

15. An intravascular catheter as in claim 10, wherein the outer layer comprises a polymer tube having a gradient durometer.

16. An intravascular catheter as in claim 10, wherein the inner layer extends proximally into the transition region.

17. An intravascular catheter as in claim 16, wherein the inner layer extends proximally into the proximal portion.

* * * * *